United States Patent
Paradies

[19]

[11] Patent Number: 5,604,206
[45] Date of Patent: Feb. 18, 1997

[54] COMPLEXES CONTAINING S(+) PHENYL ALKANE ACIDS AND AMINO SUGARS

[75] Inventor: Henrich H. Paradies, Iserlohn, Germany

[73] Assignee: Medice Chem.-Pharm. Fabrik Putter GmbH & Co. KG, Iserlohn/Westfalen, Germany

[21] Appl. No.: 328,722

[22] Filed: Feb. 18, 1994

Related U.S. Application Data

[63] Continuation of Ser. No. 792,479, Nov. 15, 1991, abandoned.

[30] Foreign Application Priority Data

Nov. 15, 1990 [DE] Germany .......................... 40 36 460.7

[51] Int. Cl.[6] .............................. A61K 31/70; C07H 5/04; C07H 5/06
[52] U.S. Cl. ............................. 514/23; 514/62; 536/18.7; 536/55.2
[58] Field of Search .............................. 536/18.7, 55.2; 514/23, 62

[56] References Cited

U.S. PATENT DOCUMENTS

| | | | |
|---|---|---|---|
| 4,501,727 | 2/1985 | Armitage et al. | 424/433 |
| 4,748,174 | 5/1988 | Veronesi | 514/226.5 |
| 4,800,162 | 1/1989 | Matson | 435/280 |
| 4,851,444 | 7/1989 | Sunshine et al. | 514/570 |

FOREIGN PATENT DOCUMENTS

3700172A1  7/1987  Germany .......................... C07H 5/06

OTHER PUBLICATIONS

M. Windholz et al, "The Merck Index" Published 1983, 10th Edition, by Merck & Co., Inc., (N.J), see pp. 636 & 637.
Chem. Abstracts, vol. 102, p. 336, 1985.

*Primary Examiner*—John Kight
*Assistant Examiner*—Everett White
*Attorney, Agent, or Firm*—Townsend and Townsend and Crew LLP

[57] ABSTRACT

New complexes of S(+)-ibuprofen and amino sugars are described. These complexes are particularly suitable for the treatment of inflammations and pains.

14 Claims, 2 Drawing Sheets

COMPLEXES CONTAINING S(+) PHENYL ALKANE ACIDS AND AMINO SUGARS

This is a Continuation of application Ser. No. 07/792,479, filed Nov. 15, 1991, now abandoned.

The present invention relates to hydrogen-bridge-bound complexes having a stoichiometry of 1:1 of S(+)-phenyl alkane acids and amino sugars.

As prior art attention is drawn to CA, 1985, 102, 225, 919 and DE-OS 2,103,387.

Further observations will be made below on this DE-OS 2,103,387.

SUMMARY OF THE INVENTION

One problem underlying the present invention is to provide new substances on the basis of S(+)-phenyl alkanoic acids and amino sugars and develop their advantageous use in pharmaceutical preparations.

This problem is solved according to the invention by hydrogen-bridge-bound complexes having a stoichiometry of 1:1 comprising S(+)-phenyl alkanoic acids and amino sugars in which the complex bond is based on interactions of the carboxyl group of the S(+)-phenyl alkane acids and the hydroxyl group at the carbon atom ($C_3$) of the amino sugars having a proton switch of the form

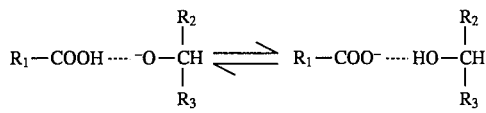

wherein $R_1$-COOH denotes the S(+)-phenyl alkanoic acids and

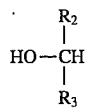

denotes the amino sugars, the pKa values relating to the carboxyl group of the S(+)-phenyl alkanoic acids lying in the range of 3.5–3.9 and the pKa values relating to the hydroxyl group at the carbon atom ($C_3$) of the amino sugars lying in the range of 1.9–4.0.

DETAILED DESCRIPTION OF THE INVENTION AND PREFERRED EMBODIMENTS

Figure 1:
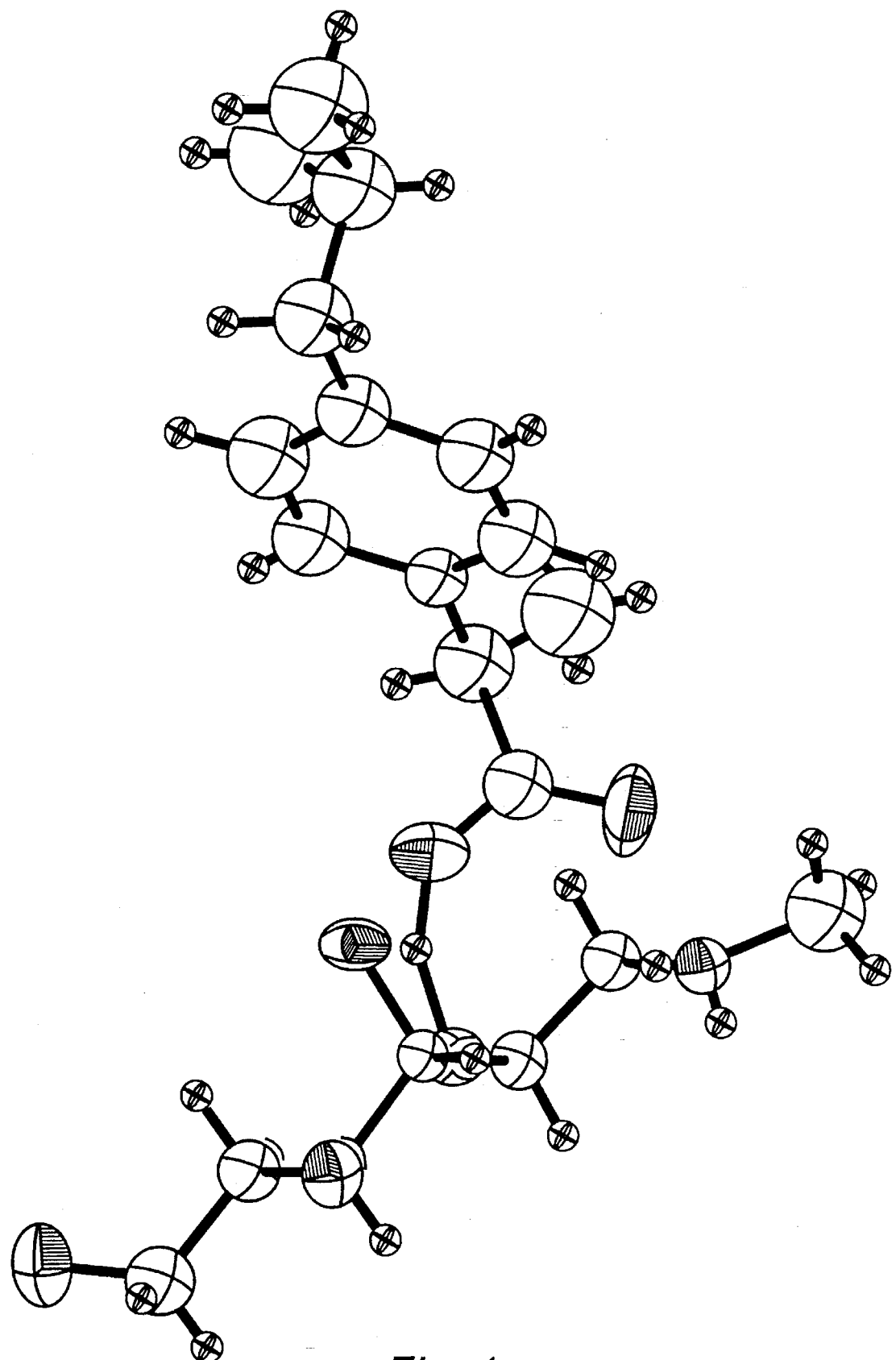
FIG. 1 is a drawing representing a complex of R(−)-ibuprofen and α-D-glucamine, derived from X-ray structure analysis.

Preferably, as S(+)-phenyl alkanoic acids herein S(+)-ibuprofen or S(+)-naproxen shall be understood and are used.

Preferably as S(+)-phenyl alkanoic acids herein the substances as detailed below shall be understood and are used. These substances comprise the following structure:

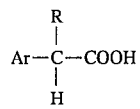

in which R is lower alkyl, Ar is preferably a monocyclic, polycyclic or ortho-condensed polycyclic aromatic group having up to twelve carbons in the aromatic system, e.g. phenyl, diphenyl, and naphthyl. The substituents of these aromatic groups comprise one or more halogen atoms, $C_1$–$C_4$ alkyls, benzyl, hydroxy, $C_1$–$C_2$ alkoxy, phenoxy and benzoyl groups. Examples of such substituted aryls are: 4-isobutyl-phenyl, 3-phenoxy-phenyl, 2-fluoro-4-diphenyl, 4'-fluoro-4-diphenyl, 6-methoxy-2-naphthyl, 5-chloro-6-methoxy-2-naphthyl and 5-bromo-6-methoxy-naphthyl, 4-chloro-phenyl, 4-difluoro-methoxyphenyl, 6-hydroxy-2-naphthyl, and 5-bromo-6-hydroxy-2-naphthyl.

Preferably, the amino sugars have the following general formula:

where
R=hydrogen, methyl or ethyl and
Z=the skeleton of the amino sugar, which contains 5 or 6 carbon atoms.

Preferably, the amino sugar is linear or cyclic.

Preferably, the amino sugar is a penrose or hexose derivative, in particular glucamine, N-methyl glucamine, N-ethyl glucamine, ribamine, preferably in the D-form, and the epimers of the hexosamines, in particular allosamine, altrosamine, glucosamine, mannosamine, gulosamin idosamine, galactosamine and talosamine and the pentoseamine, in particular ribosamine, arabinosamine, xylosamine and lyxosamine.

Preferably, the amino sugars are present in the D-form.

According to the invention the complexes of the invention are prepared by the following method steps:

a) for the preparation from aqueous medium (only water) or weakly buffered aqueous solutions covering a pH range between pH 5.5–7.5 (20° C.) a buffered aqueous solution, for example a 0.01M–0.001M-$K_2HPO_4$/$KH_2PO_4$ buffer pH 6.0–7.5 (20° C.) is prepared and into it an equivalent amount S(+)-phenyl alkanoic acid is introduced with constant stirring;

b) the solution is heated with constant stirring to 40° C. (water bath) until a clear transparent solution is obtained (normally after 20 minutes) and all the S(+)-phenyl alkane acid has gone into solution;

c) thereafter the pH of the solution is adjusted to pH 5.5–6.0 by addition of diluted phosphoric acid ($H_3PO_4$) (20° C.) and then the equivalent (corresponding) amount of the amino sugar is introduced with constant stirring;

d) the complex formation is terminated after 20 minutes, whereupon after cooling to 0°–4° C. the complexes precipitate in crystalline form and can be separated from the mother liquor via a sintered glass funnel or glass filter (1G4);

e) alternatively to method step d) the clear solution can be reduced in a rotary evaporator (water bath temperature 25°–30° C.) in the water jet vacuum to half the volume, whereupon a colourless (amorphous) deposit forms which is filtered off via a 1G4 glass filter and can be recrystallized from water/ethanol (70/30 V/V) or from ethyl acetate (100%).

The substances according to the invention do not involve a salt formation between an acidic group (carboxyl group of the ibuprofen) and a basic radical of the amino sugars, but as shown by X-ray structure analysis and FT-IR spectra, involve carboxylate-carboxyl interactions, the two carboxyl radicals of the amino sugar and for example of the ibuprofen sharing a proton. This means that the complex is formed in accordance with the X-ray structure analysis by a hydrogen bridge.

The complexes according to the invention can advantageously be used in pharmaceutical preparations containing one or more complexes and possibly optionally additionally physiologically compatible usual extenders or carriers.

Particularly advantageous is a pharmaceutical preparation on the basis of phenyl alkanoic acids having anti-inflammatory, antipyretic, antimicrobial and analgesic effect, containing an active substance complex comprising a phenyl alkanoic acid and an amino sugar and possibly additionally usual physiologically compatible and auxiliary substances, in which the active substance complex consists of S(+)-phenyl alkanoic acids and amino sugars.

Particularly advantageous is pharmaceutical preparation on the basis of ibuprofen or naproxen with anti-inflammatory, antipyretic, antimicrobial and analgesic effect, containing an active substance complex comprising an ibuprofen or naproxen and amino sugars and possibly additionally usual physiologically compatible auxiliary substances, in which the active substance complex consists of S(+)-ibuprofen or S(+)-naproxen and an amino sugar and represents an amount by weight of 0.1 to 90% (w/w) of the composition.

Particularly advantageous is a pharmaceutical composition containing 50 to 800 mg, preferably 100 to 600 mg, in particular 100 to 300 mg S(+)-ibuprofen or S(+)-naproxen.

Particularly advantageous is a pharmaceutical preparation in which the suitable dose for oral or parenteral administration is in the range of 50 to 1200 mg daily, normally between 100 and 800 mg daily, preferably between 200 and 600 mg S(+)-ibuprofen daily and the suitable doses for a topical administration of the complex lies in the range of 10–200 mg daily.

Hereinafter, the "pharmaceutically active compound" in the broader sense is denoted as a complex. In medical use said pharmaceutically active compound may be administered orally, rectally, parenterally or topically, in particular however orally or topically. Thus, the therapeutical composition of the present invention may be any pharmaceutical preparation known per se for oral, rectal, parenteral or topical administrations. Pharmaceutically usual carriers which can be used in such pharmaceutical compositions are frequently described in pharmacy. The composition of this invention may correspond to 0.1–90% (w/w) of the active compound. The compositions represent normal unitary dosage forms. These dosage forms contain 50–800 mg, preferably 100–600 mg or 100–300 mg, S(+)ibuprofen.

Oral administration forms according to the invention are preferred, such as tablets, capsules, syrup and aqueous or oily suspensions. Tablets may for example be prepared by mixing the active compound with inert extenders such as for example calcium phosphate in the presence of a disintegrating agent, for example starch, or lubricant, for example magnesium stearate, with subsequent conversion to tablet form in the normal production sense. The tablets may be prepared in the form of a retard formulation of the active compound by known methods. If desired, such tablets may be prepared by correspondingly known methods so that they do not disintegrate in the stomach, for example with the aid of cellulose, acetate, phthalate. Correspondingly, capsules may be made, for example soft or hard gelatin capsules, which contain the pharmaceutically active compound alone or in the presence of added auxiliary agents. These capsules may be made by conventional pharmaceutical technology, with or without stomach-resistant coating. Other compositions for oral administration include aqueous solutions containing the active pharmaceutical compound in the presence of a nontoxic suspension agent, for example carboxymethyl cellulose and oily suspensions which contain the active pharmaceutical compound in the presence of a vegetable oil.

In accordance with this invention pharmaceutical formulations may be employed for topical administration of the active pharmaceutical compound. The pharmaceutically active compound in this case is dispersed in a pharmaceutically suitable cream, ointment or gel. A suitable cream can for example be prepared in that the active pharmaceutical compound is dispersed in a topical carrier, for example readily volatile paraffin in an aqueous medium with the aid of surfactants (detergents). An ointment can for example be prepared by mixing the pharmaceutically active compound with a topical carrier, for example mineral oil or paraffin or beeswax. A gel-like formulation can be prepared by mixing an active pharmaceutical compound with a topical carrier, for example Carbomer BP, in the presence of water. Topically administratable compositions may consist inter alia of a matrix which is able to disperse the active pharmaceutical compound in such a manner that the latter is administered transdermally by its close contact with the skin. A suitable transdermal composition may be prepared inter alia by mixing the pharmaceutically active compound with a topical carrier, as described above, together with a possible transdermal accelerator, for example dimethyl sulfoxide or propylene glycol.

Pharmaceutical formulations in accordance with this invention which are suitable for rectal administration are inter alia suppositories on the basis of polyethylene glycol or cocoa butter.

Pharmaceutical formulations for parenteral administration contain known pharmaceutical formulations, for example sterile suspensions or sterile solutions in a suitable solvent.

In some specific pharmaceutical formulations it appears expedient to have the pharmaceutical active compounds in the size of small particles, for example colloidal solutions or particulate suspensions of the order of magnitude of 0.1–1 µm (colloid mill).

If desired, in accordance with this invention compositions may also be prepared with other compatible pharmaceutical active substances.

These complexes according to the invention have anti-inflammatory, antipyretic and interesting antimicrobial properties as well as analgesic effects. These complexes have inter alia the advantage that after oral administration after a relatively short time they result in a substantially higher plasma level of S(+)-ibuprofen than S(+)-ibuprofen in the form of the free acid. These complexes are therefore particularly important in practice for treating acute pain; rapid onset with immediate freedom from pain can be achieved. The treatment of inflammations and pain is particularly important in rheumatic patients exhibiting indications such as primary chronic polyarthritis, arthridites of rheumatic origin, articular rheumatism and muscle rheumatism with their corresponding degrees of severity. These new complexes are particularly valuable for relieving pain, for example headache, dysmenorrhea, postoperative pain, postpartum pain and pain related to influenza and colds.

Accordingly, the invention describes in particular another aspect for treating pain or inflammatory fever after administering a therapeutically effective dose of said complex. Although the exact dose of the pharmaceutically active compound depends on a number of parameters, for example age of the patient, state of the patient, case history and compliance, a suitable dose both for oral and parenteral administrations of S(+)-ibuprofen complex is in the range of 50–1200 mg daily, normally between 100 and 800 mg daily, preferably between 200 and 600 mg S(+)-ibuprofen daily administered at one time or at several times.

With topical administration of this complex the corresponding dose lies in the range of 10–200 mg daily, generally being 20–100 mg daily, as ordered by the physician.

Following features of the invention will be apparent from the following description of examples of embodiment:

EXAMPLE 1

Preparation of complexes between S(+)-ibuprofen and 1-amino-1-desoxy-D-glucitol 206.27 (250.0) mg S(+)-ibuprofen and 236.72 (181.19) mg 1-amino-1-desoxy-D-glucitol are dissolved in 6 ml water and thereafter treated with ultrasonic radiation at 45° C. for one hour. The clear solution can be stored and used after sterilization for medical purposes. The complex can be crystallized out of the ethereal or the alcoholic solution by adding said solvent at 20° C. with constant stirring to an aqueous solution of S(+)-ibuprofen and 1-amino-1-desoxy-D-glucitol (pH 7.5). The microcrystalline precipitate can be collected by filtration with subsequent drying over $CaCl_2$ under an $N_2$ atmosphere. If no crystalline forms are desired the microcrystalline precipitate can additionally be centrifuged and the supernatant is discarded and the precipitate dried over $P_2O_5/CaCl_2$ at 30° C.; the melting point of the amorphous complex is 61° C. and that of the crystalline sample 59° C.; when using other precipitation solvents, for example acetone or methyl-isopropyl ketone, DMF and petroleum ether, various crystalline forms were observed and this indicates a certain degree of polymorphism of these specific complexes, with a melting point of Fp: 106.5°–107.5° C. The compounds with low melting point contain hydrate water in varying molecular stoichiometry.

EXAMPLE 2

206.3 g (1 mol) S(+)-ibuprofen and 195.2 g (1 mol) D-(−)-N-methyl glucamine are heated with 500 ml isopropanol while stirring until the mixture boils, a clear solution resulting. While stirring, 2.5 l n-hexane are added and the mixture first further stirred for 20 minutes at room temperature and then for 3 hours at 0° C. The precipitated crystals are sucked off, washed with 2×150 ml n-hexane and dried at room temperature. Yield: 398–400 g (99.1–99.6% of the theoretical), melting point 106.5°–107.5° C.

EXAMPLE 3

Preparation of a table

| Composition: | 1 tablet contains |
|---|---|
| active constituents | |
| S(+)-ibuprofen-N-methyl glucamine | 195 mg |
| = S(+)-ibuprofen | 100 mg |
| non-active constituents | |
| gelatin | 4 mg |
| crosslinked sodium carboxymethyl cellulose | 17 mg |
| magnesium stearate | 4 mg |
| weight per tablet | 220 mg |

Preparation

The gelatin is dissolved to 10% in purified water while heating (max. 40° C.) and slowly added to the active substance in the mixer with low mixing power. The granulate obtained is dried in the fluidized bed at about 40° C. and sifted via a screening machine (mesh width 1.6 mm). The dried granulate is compacted with the aid of rams (diameter 8.4 mm) to tablets of 190 mg final weight.

Advantageously, according to the invention the complexes of the invention may also be used in pharmaceutical preparations as are described in German application DE 40 15 794.6. Such isotropic solutions can be prepared by the following method steps:

a) heating of the carrier while stirring to above the melting point until an isotropic transparent liquid is present;

b) measuring the electrical conductivity and the viscosity at the temperature of the melting point to ensure the presence of an isotropic transparent liquid;

c) determination of the refractive index;

d) setting the desired concentration of the pharmaceutical active substance while observing the molar fraction, which at 37° C. must lie between 0.001 and 0.67;

e) introduction of the pharmaceutical active substance into the solvent with constant stirring;

f) stirring the mixture until the pharmaceutical active substance is dissolved and a transparent solution obtained;

g) measuring the differential refractive index increment $[(\Delta n/\Delta c)_{T/P=constant}]$ for determining the monomolecular solution and/or h) checking the native conformation and the monomolecularity of the pharmaceutical active substance in the solution by measuring the molar extinction coefficient in the UV range and taking the absorption spectrum and detection of the chiral configuration by measuring in the polarimeter and/or i) measuring the opacification to ensure a homogeneous solution and/or k) measuring the specific conductivity $[(\Omega)_{T,V=constant}]$ for controlling the ional concentration in the isotropic solution;

l) cooling the clear solution and preparing a galenic formulation;

m) further cooling of the solution to room temperature until the solution has solidified.

Figure 2:
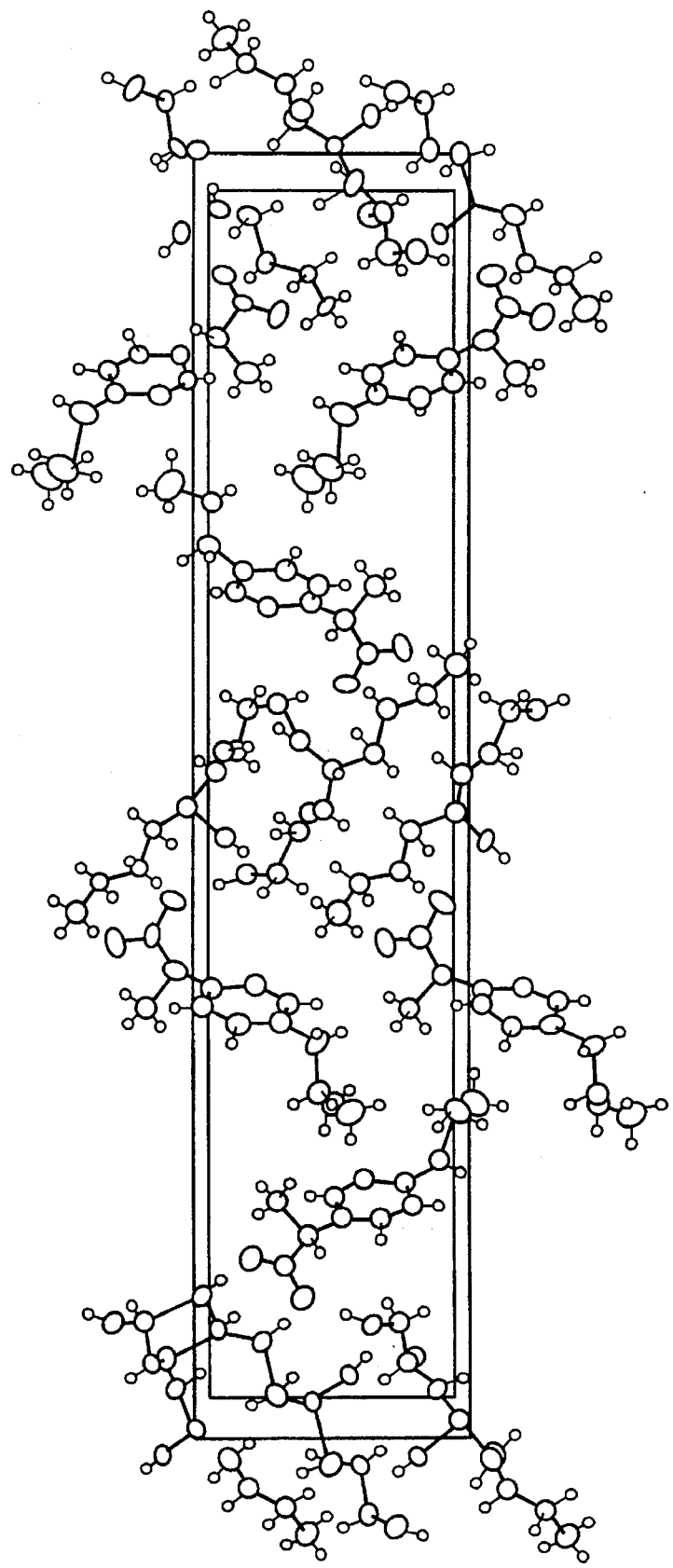
FIG. 2 is a drawing representing a complex of S(+)-ibuprofen and α-D-N-glucamine, derived from X-ray structure analysis.

In specification as laid open to inspection 2,103,387 of Aug. 17, 1972 pharmaceutical preparations are described for treating degenerative joint diseases in the combination of one or more non-steroidal antirheumatic agents, for example diphenyl butazone, monophenyl butazone, indometacine, etc., with glucose amine hydrochloride in a molar ratio of 1:10 to 10:1. In contrast to this preparation teaching, in accordance with the present novel invention a complex is formed between for example S(+)-ibuprofen and α-D-N methyl glucose amine or α-D-amino sugars in the molar ratio of S(+)-ibuprofen to α-D-amino sugar of 1:1. This complex has for example been prepared in accordance with the example disclosed (see example 2) and thereafter crystallized. The following X-ray structure analysis showed a chiralspace group with the cell dimensions a=8.275Å, b=40.872Å and c=6.520Å, space group P2$_1$2$_1$2$_1$ (#19), with four complex molecules, consisting of S(+)-ibuprofen and -N-methyl glucamine (or α-D-glucosamine) in the ratio 1:1 in the unit cell (FIG. 2). Corresponding results have also been obtained for R(−)-ibuprofen and α-D-glucamine (or α-D-glucamine or α-D-galactos amine) (FIG. 1). These structures show that a hydrogen-bridge-bound complex is involved, the carboxyl group of the S or R-ibuprofen sharing a proton with the hydroxyl group at the carbon atom (C$_3$) of the sugar, so that here we have a "proton switch" of the form

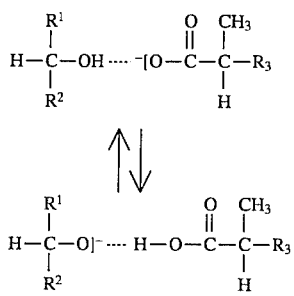

which makes the entire molecule complex appear neutral. This clearly shows that this is neither an ion pair nor salts but a 1:1 complex having a pronounced hydrogen bridge formation between the carboxo group of the S or R-ibuprofen and the O$_3$ oxygen of the N-methyl-amino-S-deoxy-D-glucitol (N-methyl-D-glucamine). As apparent from the structure, the amino group does not participate in this complex formation. This surprising finding is also in agreement with FT-IR investigations as well as with Raman spectroscopic experiments. It is moreover astonishing that this molecular complex, even with unsubstituted 2-amino-2-deoxy glucose or the stereoisomer 2-amino-2-deoxy-galactose, shows the sugar component in the open-chain form and not in its cyclic conformation, as was hitherto known. The pharmacokinetic and pharmacodynamic behaviour is very similar to that of the complexes consisting of α-D-amino acids and S(+)-ibuprofen: Rapid onset effect with $t_{max}$ of 15–20 minutes, a high AUC of 55=μg/ml×h for the same amount of active substance (150 mg). Table 1 shows all the pharmacokinetic data which are relevant and demonstrate the superiority of the sugar complex compared with the free acid.

TABLE 1

Pharmacokinetic parameters after taking a (single) oral dose of S(+)-ibuprofen-N-methyl-2-deoxy-glucitol (150 mg ibuprofen active substance) (4 test persons)
Tablet
S(+)-ibuprofen
free acid

| Mean ± SD | Tablet free acid | Sugar complex |
| --- | --- | --- |
| $t_{max}$, h | 2.1 ± 0.2 | 0.25 ± 0.11 |
| $C_{max}$, μg/ml | 10.1 ± 5.0 | 24.5 ± 6.7 |
| AUC, μg/ml × h | 40.0 ± 11.0 | 55.0 ± 10.2 |
| $t_{lag}$, h | 0.50 ± 0.1 | 0.1 ± 0.02 |
| $t_{1/2}$, h | 2.2 ± 0.3 | 1.5 ± 0.3 |

I claim:

1. A hydrogen-bridge-bound complex having a stoichiometry of 1:1 comprising an S(+)-phenyl alkanoic acid selected from the group consisting of S(+)-ibuprofen and S(+)-naproxen, the pK$_a$ of the carboxyl group of said S(+)-phenyl alkanoic acid being in the range of 3.5 to 3.9; and (b) an amine-substituted compound having a 3-position carbon atom bearing a hydroxyl group, said amine-substituted compound selected from the group consisting of glucamine, N-methyl glucamine, N-ethyl glucamine, ribamine, allosamine, altrosamine, mannosamine, gulosamine, idosamine, galactosamine, talosamine, ribosamine, arabinosamine, xylosamine and lyxosamine, the pK$_a$ value of the hydroxyl group at the 3-position carbon atom of the amino sugar being in the range of 1.9 to 4.0;

the complex bond being a protein-exchange interaction between the carboxyl group of the S(+)-alkanoic acid and the hydroxyl group at the 3-position carbon atom of the amine-substituted compound.

2. A pharmaceutical preparation comprising one or more complexes according to claim 1 and a physiologically compatible carrier.

3. A pharmaceutical preparation according to claim 2 in the form of an isotropic solution in which:

(a) said one or more complexes are dissolved in said carrier in a form which is a member selected from the group consisting of monomolecular and ionic forms;

(b) said one or more complexes is in a conformation which is a member selected from the group consisting of native and enantiomeric conformations;

(c) the molar fraction of said one or more complexes relative to said pharmaceutical preparation is from 0.001 to 0.67;

(d) said carrier is molten, phase-uniform and isotropic at body temperature;

(e) said isotropic solution solidifies at room temperature;

(f) said isotropic solution when solidified is crystalline or noncrystalline, and contains said one or more complexes in crystalline form or in a form which can be crystallized out of said solidified isotropic solution;

(g) said isotropic solution has an osmotic pressure and effects a molar freezing point reduction; and (h) said one or more complexes has a temperature-dependent diffusion coefficient and a temperature-dependent specific conductivity.

4. A pharmaceutical preparation comprising one or more complexes according to claim 1, said one or more complexes representing 0.1 to 90% by weight of said preparation.

5. A pharmaceutical preparation according to claim 4, containing from 50 to 800 mg of said S(+)-phenyl alkanoic acid.

6. A pharmaceutical preparation according to claim 4, containing from 100 to 600 mg of said S(+)-phenyl alkanoic acid.

7. A pharmaceutical preparation according to claim 4, containing from 100 to 300 mg of said S(+)-phenyl alkanoic acid.

8. A method for treating a subject suffering from pain or inflammatory fever, said method comprising administering to said subject a therapeutically effective amount of a complex according to claim 1.

9. A method in accordance with claim 8 comprising orally or parentally administering said complex at a dosage of 50 to 1200 mg daily.

10. A method in accordance with claim 8 comprising orally or parentally administering said complex at a dosage of 100 to 800 mg daily.

11. A method in accordance with claim 8 in which said S(+)-phenyl alkanoic acid is S(+)-ibuprofen, and said method comprises orally or parentally administering said complex at a dosage of 200 to 600 mg daily.

12. A method in accordance with claim 8 comprising topically administering said complex at a dosage of 10 to 200 mg daily.

13. A method for the preparation of a complex of an S(+)-phenyl alkanoic acid and amino sugar, said method comprising:

(a) combining said S(+)-phenyl alkanoic acid with an aqueous buffer solution having a pH range of 5.5 to 7.5 at 20° C.;

(b) heating the combined acid and buffer solution of step (a) to 40° C. with constant stirring until a clear transparent solution is obtained and all of said S(+)-phenyl alkanoic acid is dissolved;

(c) adjusting the pH of the solution resulting from step (b) to 5.5–6.0 by the addition of diluted phosphoric acid, then adding said amino sugar in an equimolar mount relative to said S(+)-phenyl alkanoic acid to form a reaction mixture; and (d) after complex formation is complete, cooling said reaction mixture to precipitate therefrom said complex in crystalline form, and recovering said precipitated complex from said reaction mixture.

14. A method for the preparation of a complex of an S(+)-phenyl alkanoic acid and amino sugar, said method comprising:

(a) combining said S(+)-phenyl alkanoic acid with an aqueous buffer solution having a p.H range of 5.5 to 7.5 at 20° C.;

(b) heating the combined acid and buffer solution of step (a) to 40° C. with constant stirring until a clear transparent solution is obtained and all of said S(+)-phenyl alkanoic acid is dissolved;

(c) adjusting the pH of the solution resulting from step (b) to 5.5–6.0 by the addition of diluted phosphoric acid, then adding said arnino sugar in an equimolar amount relative to said S(+)-phenyl alkanoic acid to form a reaction mixture; and (d) after complex formation is complete, evaporating solvent from said reaction mixture to leave an amorphous solid, and recovering said solid.

* * * * *